United States Patent
Ogawa et al.

(10) Patent No.: US 10,098,706 B2
(45) Date of Patent: Oct. 16, 2018

(54) OPERATION INPUT DEVICE AND MEDICAL MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/636,067

(22) Filed: Jun. 28, 2017

(65) Prior Publication Data
US 2017/0296280 A1    Oct. 19, 2017

Related U.S. Application Data

(63) Continuation of application No. PCT/JP2015/085416, filed on Dec. 17, 2015.

(30) Foreign Application Priority Data

Jan. 6, 2015    (JP) .................................. 2015-000796

(51) Int. Cl.
*A61B 34/00* (2016.01)
*A61B 34/30* (2016.01)
*B25J 3/00* (2006.01)

(52) U.S. Cl.
CPC .............. *A61B 34/74* (2016.02); *A61B 34/30* (2016.02); *A61B 34/71* (2016.02); *B25J 3/00* (2013.01);
(Continued)

(58) Field of Classification Search
CPC ......... A61B 34/30; A61B 34/71; A61B 34/74; A61B 2034/301; A61B 2034/742; B25J 3/00
See application file for complete search history.

(56) References Cited

U.S. PATENT DOCUMENTS

2003/0135204 A1* 7/2003 Lee .................... A61B 17/0469
606/1
2005/0075739 A1    4/2005 Nishizawa
(Continued)

FOREIGN PATENT DOCUMENTS

EP    2617530 A1    7/2013
EP    2 982 332 A1    2/2016
(Continued)

OTHER PUBLICATIONS

Japanese Office Action dated Aug. 17, 2016 received in JP 2016-542297.
(Continued)

*Primary Examiner* — Khoi H Tran
*Assistant Examiner* — Robert T Nguyen
(74) *Attorney, Agent, or Firm* — Scully, Scott, Murphy & Presser, P.C.

(57) ABSTRACT

Provided is an operation input device for inputting an operation command to a medical manipulator having a distal-end-side moving portion having at least one joint on a distal end and a proximal-end-side moving portion that is connected to a proximal-end side of the distal-end-side moving portion and moves the distal-end-side moving portion, and the operation input device includes a first operation portion that generates a moving command for driving the distal-end-side moving portion in accordance with an operation command input with a palm or a finger and a second operation portion that is linked to the first operation portion and generates the moving command for driving the proximal-end-side moving portion in accordance with an operation command input with a wrist or an arm.

2 Claims, 7 Drawing Sheets

(52) U.S. Cl.
CPC ... *A61B 2034/301* (2016.02); *A61B 2034/742* (2016.02)

(56) References Cited

U.S. PATENT DOCUMENTS

| | | | |
|---|---|---|---|
| 2008/0193260 A1 | 8/2008 | Yokokohji et al. | |
| 2011/0152881 A1 | 6/2011 | Conner et al. | |
| 2012/0143353 A1 | 6/2012 | Kishi | |
| 2013/0296882 A1* | 11/2013 | Kim | A61B 19/2203 606/130 |
| 2014/0195010 A1 | 7/2014 | Beira et al. | |
| 2014/0200851 A1* | 7/2014 | Weir | H02K 11/0094 702/182 |
| 2014/0222023 A1* | 8/2014 | Kim | A61B 19/2203 606/130 |
| 2016/0058514 A1 | 3/2016 | Ogawa et al. | |

FOREIGN PATENT DOCUMENTS

| | | |
|---|---|---|
| JP | 2000-350735 A | 12/2000 |
| JP | 2005-103741 A | 4/2005 |
| JP | 2006-334695 A | 12/2006 |
| JP | 2010-253162 A | 11/2010 |
| JP | 2013-049121 A | 3/2013 |
| JP | 2014-534080 A | 12/2014 |
| WO | WO 2012/073789 A1 | 6/2012 |
| WO | WO 2013/014621 A2 | 1/2013 |
| WO | WO 2014/033717 A1 | 3/2014 |
| WO | 2014/156250 A1 | 10/2014 |

OTHER PUBLICATIONS

International Search Report dated Mar. 8, 2016 issued in PCT/JP2015/085416.
Extended Supplementary European Search Report dated Aug. 2, 2018 in European Patent Application No. 15 87 7007.3.

\* cited by examiner

OPERATION INPUT DEVICE AND MEDICAL MANIPULATOR SYSTEM

CROSS-REFERENCE TO RELATED APPLICATIONS

This is a continuation of International Application PCT/JP2015/085416, with an international filing date of Dec. 17, 2015, which is hereby incorporated by reference herein in its entirety. This application claims the benefit of Japanese Patent Application No. 2015-000796, the content of which is incorporated herein by reference.

TECHNICAL FIELD

The present invention relates to an operation input device and a medical manipulator system.

BACKGROUND ART

In the related art, there is a known operation input device with which an operator inputs an operation command for manipulating an operation object having six degrees of freedom. With the operation input device, the operation command for manipulating the orientation of the operation object is input on the basis of the position and orientation of a gripping portion gripped with fingers, and the operation command for manipulating the position of the operation object is input on the basis of the position and orientation of an armrest portion operated by a portion of the arm near the wrist (for example, see PTL 1).

In addition, there is a known operation input device that allows manipulation of a remote manipulator with more degrees of freedom by providing, on an arm table, a switch that is operable in two degrees of freedom (for example, see PTL 2).

CITATION LIST

Patent Literature

{PTL 1} Japanese Unexamined Patent Application, Publication No. 2005-103741
{PTL 2} Japanese Unexamined Patent Application, Publication No. 2006-334695

SUMMARY OF INVENTION

One aspect of the present invention is an operation input device for inputting an operation command to a medical manipulator having a distal-end-side moving portion having at least one joint on a distal end and a proximal-end-side moving portion that is connected to a proximal-end side of the distal-end-side moving portion and moves the distal-end-side moving portion, the device comprising: a first operation portion that generates a moving command for driving the distal-end-side moving portion in accordance with an operation command input with a palm or a finger; and a second operation portion that is linked to the first operation portion and generates a moving command for driving the proximal-end-side moving portion in accordance with an operation command input with a wrist or an arm.

Another aspect of the present invention is a medical manipulator system comprising any of the operation input devices described above and a medical manipulator that is operated by the operation input device.

DESCRIPTION OF EMBODIMENT

An operation input device 2 and a medical manipulator system 1 according to one embodiment of the present invention will be described below with reference to the drawings.

Figure 1:
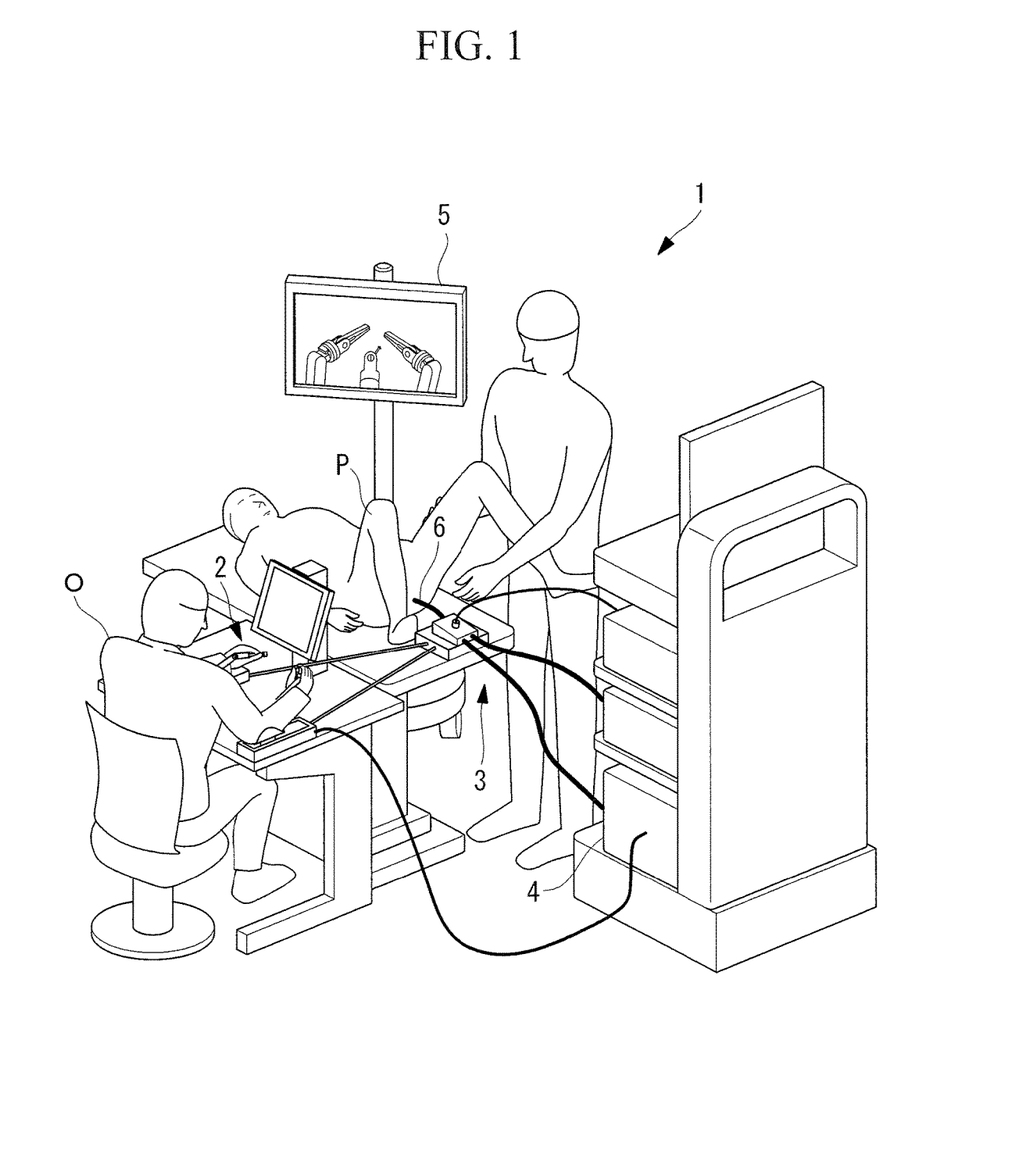
FIG. 1 is an overall configuration diagram showing a medical manipulator system according to one embodiment of the present invention.

As shown in FIG. 1, the medical manipulator system 1 according to this embodiment includes operation input devices 2 that are operated by an operator O, a medical manipulator 3 that is inserted into a body cavity of a patient P, a controller 4 that controls the medical manipulators 3 according to the operation performed on the operation input devices 2, and a monitor 5.

Figure 2:
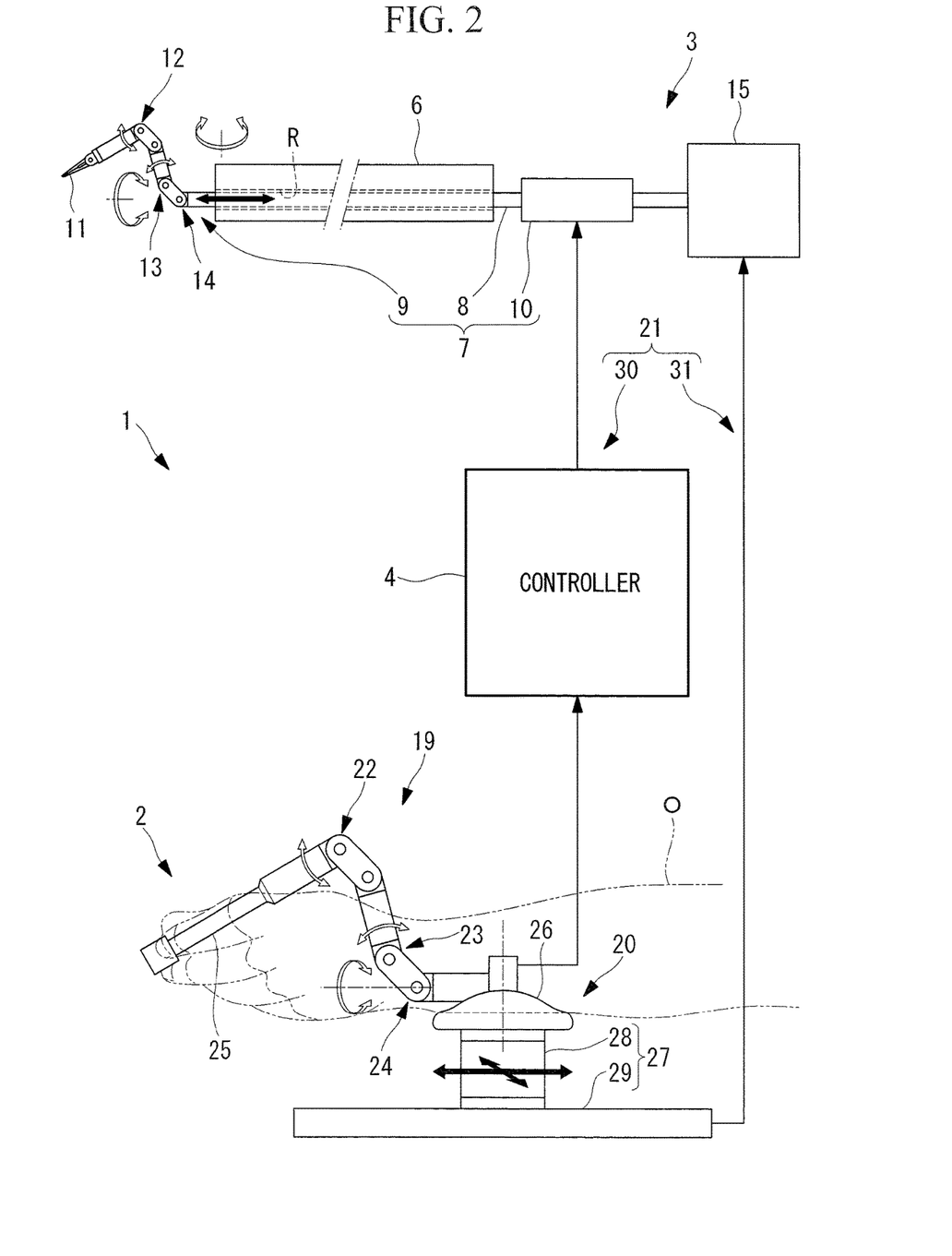
FIG. 2 is a diagram showing medical manipulator, an operation input device, and a controller used in the medical manipulator system shown in FIG. 1.

As shown in FIG. 2, the medical manipulator 3 includes, for example, an insertion portion 6 that is inserted into the body cavity of the patient P and two distal-end-side moving portions 7 that are inserted into the body of the patient P through channels R formed so as to pass through the insertion portion 6 in the longitudinal direction. Each of the distal-end-side moving portions 7 has an elongated portion 8 that is disposed in the channel R so as to be movable in the longitudinal direction, a movable portion 9 that is provided on a distal end of the elongated portion 8, and a distal-end driving unit 10 that is disposed at the proximal-end side of the elongated portion 8 and drives the movable portion 9 with motive-force transmitting members, such as wires etc. (not shown). The distal-end driving unit 10 includes an electrical driving source (not shown), such as a motor etc., for applying tension to the wires in accordance with a moving command from the controller 4.

Figure 4:
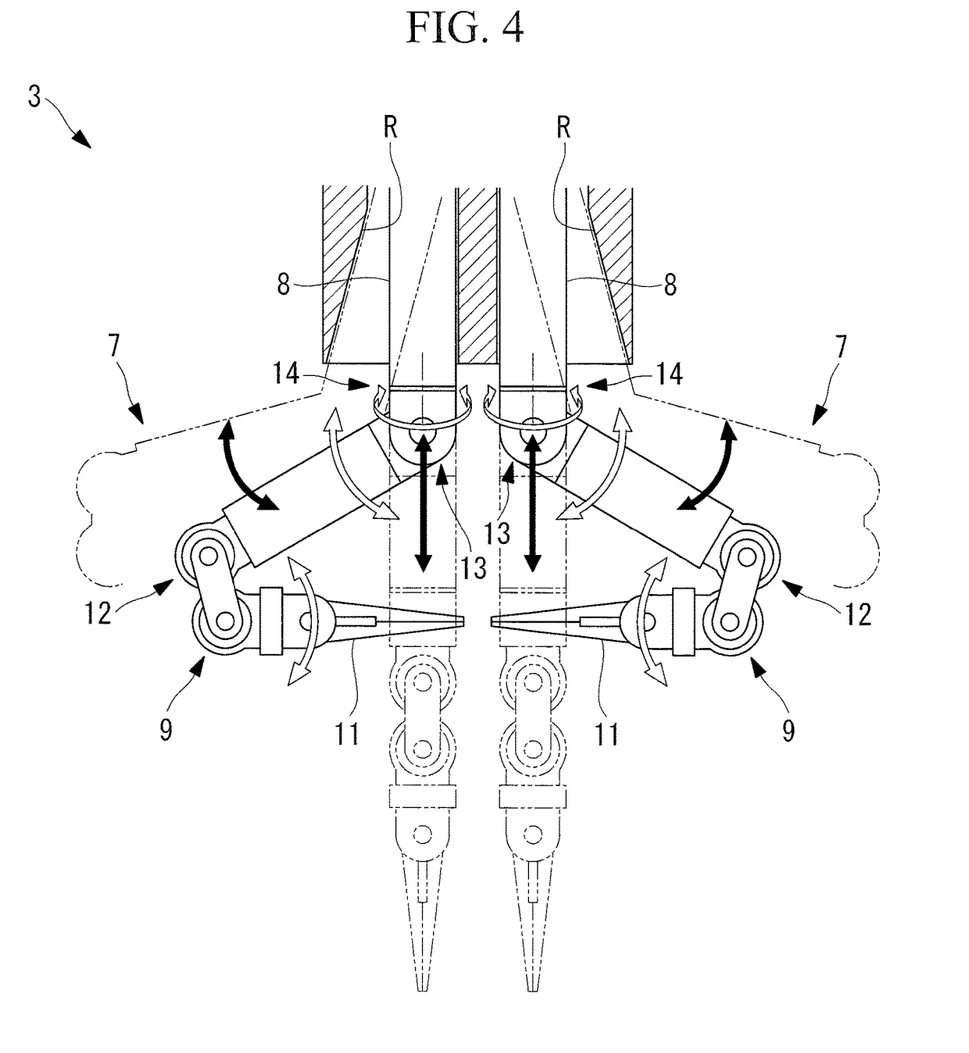
FIG. 4 is a diagram showing an example of movable portions of the medical manipulator provided in the medical manipulator system shown in FIG. 1.

As shown in FIG. 4 with open arrows, each of the movable portions 9 has two joints 12 and 13 that allow a treatment portion 11, such as gripping forceps etc., disposed at the distal end to swing about two parallel axes and a joint 14 that allows the treatment portion 11 to rotate about the longitudinal axis of the elongated portion 8. Each of the movable portions 9 is configured such that the distal end position of each of the gripping forceps 11 can be set in three dimensions through movement of these three joints 12, 13, and 14.

The joint 14 may be configured as a torque tube having superior rotational force transmitting properties so as to be able to rotate the entire elongated portion 8. By having such a configuration, it is possible to rotate the elongated portion 8 about the longitudinal axis thereof with ease. In this case, the elongated portion 8 itself is electrically driven in a precise manner.

In addition, the medical manipulator 3 includes, on the proximal-end side of the respective distal-end-side moving portions 7, two proximal-end-side moving portions 15 that are connected to the distal-end-side moving portions 7, respectively, and thereby, the respective distal-end-side moving portions 7 are advanced and retracted in the longitudinal direction of the insertion portion 6 and, in the vicinity of the distal end of the insertion portions 6, the elongated portions 8 are curved in the direction orthogonal to the longitudinal direction.

Figure 3:
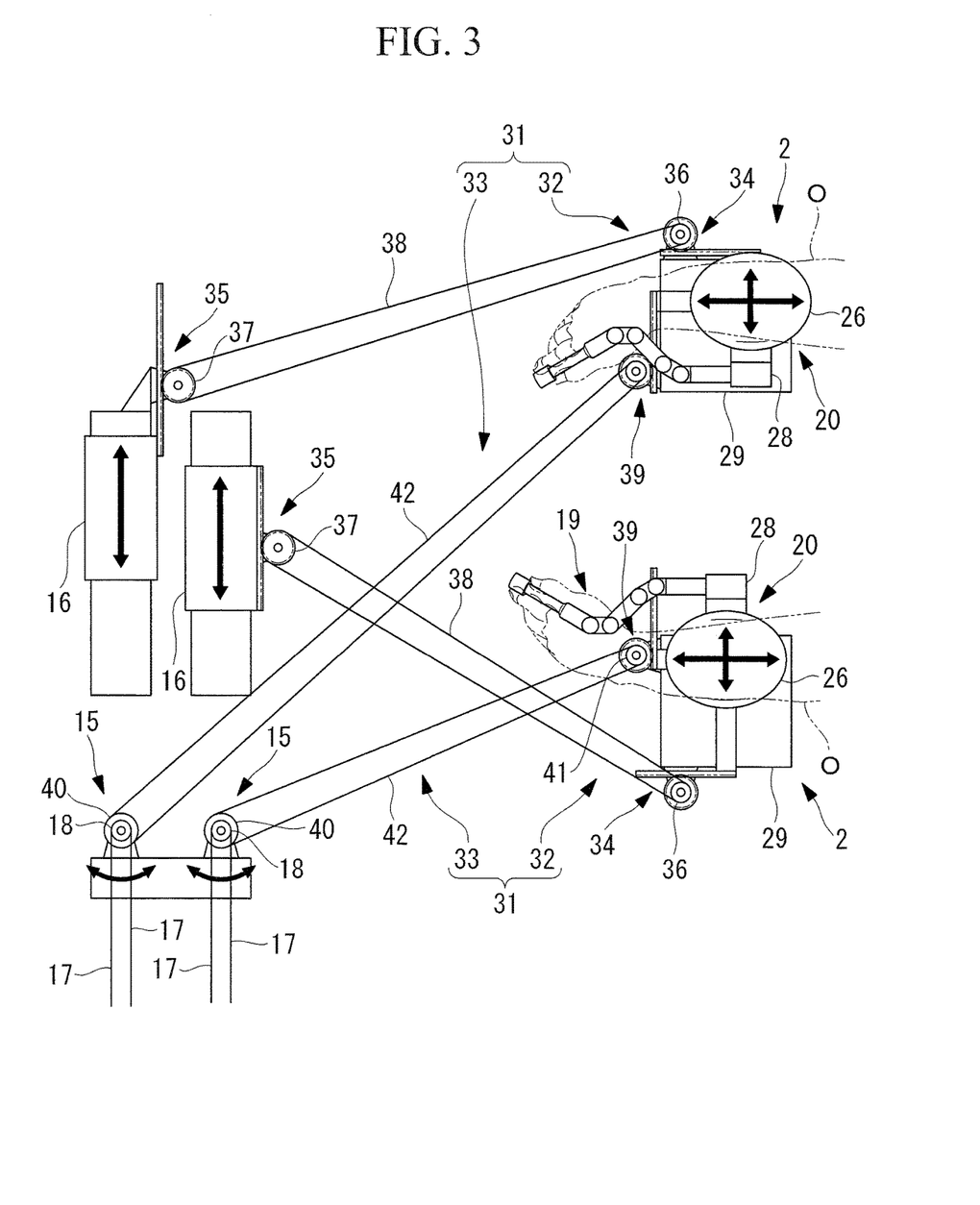
FIG. 3 is a plan view for explaining a second operation portion, a command transmitting portion, and a proximal-end-side moving portion of the operation input device of the medical manipulator system shown in FIG. 1.

As shown in FIG. 3, each of the proximal-end-side moving portions 15 includes a slider 16 to which the proximal-end side of each of the distal-end-side moving portions 7 is fixed. The sliders 16 are provided so as to be movable in the longitudinal direction of the insertion portion 6. In addition, each of the proximal-end-side moving portions 15 includes two wires 17 one ends of which are fixed to the elongated portion 8 in the vicinity of the distal end thereof and a pulley 18 at which the proximal ends of the wires 17 are fixed. By pulling the two wires 17 in an alternating manner by rotation of the pulley 18, the elongated portion 8 is curved in the direction orthogonal to the longitudinal direction in the vicinity of the distal end of the insertion portion 6.

As shown in FIGS. 2 and 3, each operation input device 2 according to this embodiment includes a first operation portion 19 that is operated by being gripped by the hand of the operator O, a second operation portion 20 that is operated by the wrist or arm of the operator O, and a command transmitting portion 21 that transmits the operation commands input by these operation portions 19 and 20 to the medical manipulator 3.

The first operation portion 19 is configured to have a similar shape as that of the movable portion 9 of the medical manipulator 3 such that distal end portion 25, which is supported by the same number of joints 22, 23, and 24 as that of the movable portion 9, is gripped by the hand of the operator O and is moved by the palm or fingers. The first operation portion 19 includes sensors (not shown) for respectively detecting the angles of the joints 22, 23, and 24 forming the first operation portion 19.

The sensors are configured so as to generate electrical signals corresponding to the angles of the respective joints 22, 23, and 24. By doing so, in the first operation portion 19, it is possible to input the operation command with the palm or fingers of the operator O and generate moving commands formed of the electrical signals.

The second operation portion 20 includes an arm supporting table 26 that is attached to base portion of the first operation portion 19 and a linear motion mechanism 27 that supports the arm supporting table 26 and the first operation portion 19 in a manner allowing integral movement. The arm supporting table 26 is disposed at a position on which a portion of the arm near the wrist of the hand gripping the distal end portion 25 is placed when the operator O grips the distal end portion 25 of the first operation portion 19.

The linear motion mechanism 27 includes a slider 28 to which the arm supporting table 26 and the first operation portion 19 are fixed, and a linear guide 29 that supports the slider 28 so as to be movable in two mutually orthogonal horizontal directions, as shown with solid arrows in FIGS. 2 and 3. The slider 28 is moved in the horizontal directions by the arm supported on the arm supporting table 26, and thereby, it is possible to move the position of the first operation portion 19 while maintaining the gripping state of the first operation portion 19. Thus, with the second operation portions 20, by inputting the operation commands with the wrists or arms of the operator O, it is possible to transform the force input by the wrists or arms to mechanical driving force generated by the two sliders 28.

The command transmitting portion 21 includes an electrical-signal transmitting portion 30 that connects the first operation portions 19 to the distal-end driving unit 10 and mechanical-motive-force transmitting portions 31 that respectively connect the second operation portions 20 to the proximal-end-side moving portions 15.

In the electrical-signal transmitting portion 30, the moving commands formed of the electrical signals generated in the first operation portions 19 are transmitted to the controller 4, and command signals generated by the controller 4 are supplied to respective motors of the distal-end driving unit 10. The controller 4 controls the respective motors of the distal-end driving unit 10 by calculating the amount of rotational movement and rotational speed of each motor on the basis of the moving commands generated in the first operation portions 19.

As shown in FIG. 3, the mechanical-motive-force transmitting portions 31 include: first transmitting portions 32 that convert the translational movement in the first direction in which the respective sliders 28 of the operation input devices 2 are moved forward and backward into the translational movement of the respective sliders 16 of the proximal-end-side moving portions 15; and second transmitting portions 33 that convert the translational motion in the left-right direction orthogonal to the first direction of the respective sliders 28 of the operation input devices 2 into the rotation angles of the respective pulleys 18 of the proximal-end-side moving portions 15.

The first transmitting portions 32 include first rack-and-pinion mechanisms 34 that convert the amount of translational motion, in the first direction, of the sliders 28 of the operation input devices 2 into rotation angles, second rack-and-pinion mechanisms 35 that convert the rotational movement to the amount of translational motion of the proximal-end-side moving portions 15, pulleys 36 and 37 that are respectively fixed to pinion gears of the rack-and-pinion mechanisms 34 and 35, and belts 38 that are placed between the pulleys 36 and 37.

The second transmitting portions 33 include first rack-and-pinion mechanisms 39 that convert the amounts of translational motion, in the second direction, of the sliders 28 of the operation input devices 2 into rotation angles, pulleys 40 that are fixed to the pulleys 18 of the proximal-end-side moving-portions 15, pulleys 41 that are respectively fixed to pinion gears of the first rack-and-pinion mechanisms 39, and belts 42 that are placed between the pulleys 40 and 41.

The operation of the thus-configured operation input devices 2 and medical manipulator system 1 according to this embodiment will be described below.

In order to carry out treatment of an affected part in the body of the patient P by using the medical manipulator system 1 according to this embodiment, the insertion portion 6 of the medical manipulator 3 is inserted into the body cavity of the patient P, and the movable portions 9 and the elongated portions 8 are inserted into the body of the patient P through the channels R in the insertion portion 6.

In a state in which the movable portions 9 are disposed in the vicinity of the affected part in the body cavity, the operator O operates the operation input devices 2 while checking an image acquired by an endoscope (not shown) on the monitor 5. In order to operate the operation input devices 2, as shown in FIG. 3, the operator O grips the distal end portions 25 of the two first operation portions 19, forming a pair, with both hands, respectively, and places the portions of the arms near both hands on the arm supporting tables 26 of the two second operation portions 20, forming a pair, respectively.

When the operator O applies a force to the arm supporting table 26 with either of the arms, the slider 28 on which the arm supporting table 26 is fixed is moved in the direction in which the force is applied, the amount of motion is resolved into the amount of translational motion in the forward/backward direction and the amount of translational motion in the left-right direction, and the resolved components are respectively converted into rotation angles by the first rack-and-pinion mechanisms 34 and 39.

The amount of translational motion, in the first direction, of the first rack and pinion mechanism 34, which has been converted into a rotation angle, is transmitted to the second rack-and-pinion mechanism 35 through the pulleys 36 and 37 and the belt 38, and it is converted into the amount of translational motion of the slider 16 of the proximal-end-side moving portion 15. Because the slider 16 is fixed to the distal-end-side moving portion 7, the movable portion 9, the elongated portion 8, and the distal-end driving unit 10 forming the distal-end-side moving portion 7 is moved integrally along the longitudinal direction of the elongated portion 8. Thereby, the distal end position of the gripping forceps 11 located at the distal end of the movable portion 9 is manually moved roughly in the forward/backward direction.

The amount of translational motion, in the second direction, of the first rack-and-pinion mechanism 39, which has been converted into a rotation angle, is converted into the rotation angle of the pulley 18 of the proximal-end-side moving portion 15 through the pulleys 40 and 41 and the belt 42. Because the two wires 17 are fixed to the pulley 18, the tension applied to one of the wires 17 is increased as the pulley 18 is rotated in one direction and the distal end of the elongated portion 8 is pulled, and the elongated portion 8 is swung in the direction orthogonal to the longitudinal direction thereof. Thereby, the distal end position of the gripping forceps 11 located at the distal end of the movable portion 9 is manually moved roughly in the left-right direction.

On the other hand, when the operator O moves the distal end portions 25 of the first operation portions 19 gripped in both hands with forces exerted by the palms or fingers, the displaced amounts are detected by the sensors respectively provided on the joints 22, 23, and 24 and are transmitted to the controller 4 in the form of electrical signals. In the controller 4, electrical moving commands are calculated so as to move the joints 12, 13, and 14 of the movable portions 9 such that their angles respectively match those of the joints 22, 23, and 24 detected by the sensors, and the electrical moving commands are supplied to the motors respectively connected to the joints 12, 13, and 14. Thereby, the distal end positions of the gripping forceps 11 provided on the distal end of the movable portions 9 are electrically moved precisely as instructed with the palms or fingers.

With the operation input device 2 and the medical manipulator system 1 according to this embodiment, the following advantage is afforded because the first operation portion 19 that sets the final distal end position of the gripping forceps 11 is separated from the second operation portion 20 that roughly sets the position of the entire distal-end-side moving portion 7, and it is operated with a different part of the hand, such as the palm or fingers and the wrist or the arm.

Specifically, because the long, thin elongated portions 8 need to be moved within the channels R, the movement resolution of the advancing/retracting movement of the entire distal-end-side moving portions 7 is low due to friction. In contrast, the resolution of the movement of the movable portions 9 is high because the effect of the friction is small. Therefore, by moving the movable portions 9 by means of the first operation portions 19, it is possible to more precisely set the distal end positions of the gripping forceps 11.

In other words, by separating the operation of the second operation portion 20 using the wrist or arm for roughly moving the entire distal-end-side moving portion 7 from the operation of the first operation portion 19 using the palm or fingers, which requires more precise operation, no confusion is caused between two operational inputs, and the operations can be performed without an unintuitive feeling. In addition, because the separation is achieved between two parts of the hand, namely, the distal-end side of the wrist and the proximal-end side of the wrist, an advantage is afforded in that the operation can be performed intuitively in accordance with the operational resolution of the human hand.

In addition, with the operation input devices 2 and the medical manipulator system 1 according to this embodiment, the following advantage is afforded because an operation portion that generates electrical signals for electrically driving the movable portion 9 is employed as the first operation portion 19, and an operation portion that generates mechanical driving forces for manually driving the entire distal-end-side moving portion 7 is employed as the second operation portion 20.

In other words, because the movable portions 9 are electrically driven by the precise operation of the first operation portions 19 with the palms or fingers, it is possible to precisely set the positions of the distal end portions of the gripping forceps 11. On the other hand, because a portion with which the distal-end-side moving portions 7 undergo a large-scale movement is manually operated via a rough operation of the second operation portions 20 with the wrists or arms, an advantage is afforded in that it is possible to easily recognize, with the wrists or arms, a repulsive force generated by contact between the movable portions 9 and the surrounding tissue etc.

In this embodiment, although a configuration including two swinging joints 12 and 13 that are provided on the distal-end side and have substantially parallel axes and one rotating joint 14 that is provided on the proximal-end side and rotates about the longitudinal axis of the elongated portion 8 is illustrated as the movable portion 9, the configuration is not limited thereto, and any axial configuration that achieves three degrees of freedom to allow movement of the distal end position of the gripping forceps 11 in three dimensions may be employed. In addition, the rotating joint 14 may be provided on the proximal-end side of the elongated portion 8. Furthermore, the movable portion 9 may include another joint in order to increase the movable range to ensure redundancy.

In addition, in this embodiment, although a case in which the first operation portion 19 and the movable portion 9 have similar shapes to each other is illustrated, instead of this configuration, another input device of any kind having a non-similar shape (for example, a device with different configuration or a remote-control device) may be employed.

In addition, it is preferable that the arm supporting table 26 of the second operation portion 20 be disposed at positions one level lower with respect to the first operation portion 19 such that the arm can be naturally placed when the distal end portion 25 of the first operation portion 19 is held like a pen. A position adjusting mechanism for adjusting the position of the arm supporting table 26 may also be provided. In addition, two arm supporting table 26 may be disposed so as to face each other at the inner sides. With such a configuration, it is possible to place the arms in a natural orientation and to facilitate the operation.

Figure 5:
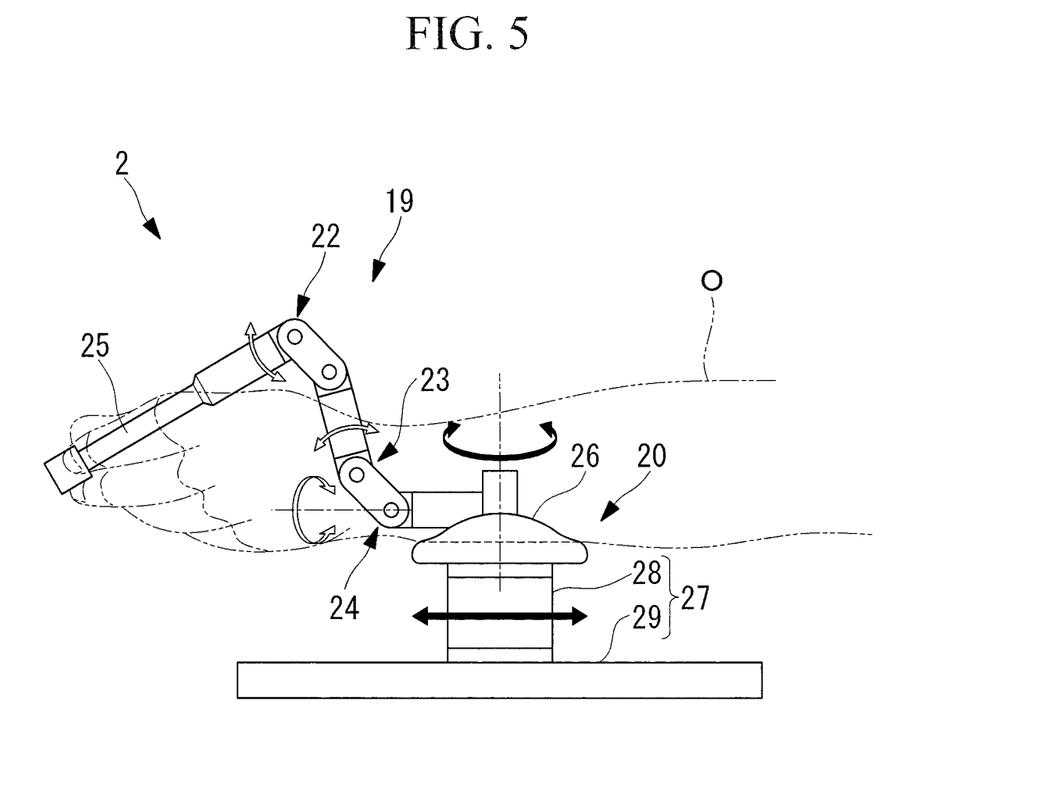
FIG. 5 is a front view showing a modification of the operation input device shown in FIG. 2.

In addition, although a configuration in which the sliders 28 are provided so as to be movable in two mutually orthogonal directions is illustrated as the second operation portions 20, instead of this configuration, as shown in FIG. 5, the operation input in two directions may be achieved by the advancing/retracting direction and the horizontal rotation of the arm supporting table 26. With the axial configuration in which the distal ends of the elongated portions 8 swing around as shown in FIG. 4, an advantage is afforded in that the operation can be performed more intuitively with a configuration shown FIG. 5 in which the arm supporting table 26 is rotated horizontally.

Figure 6:
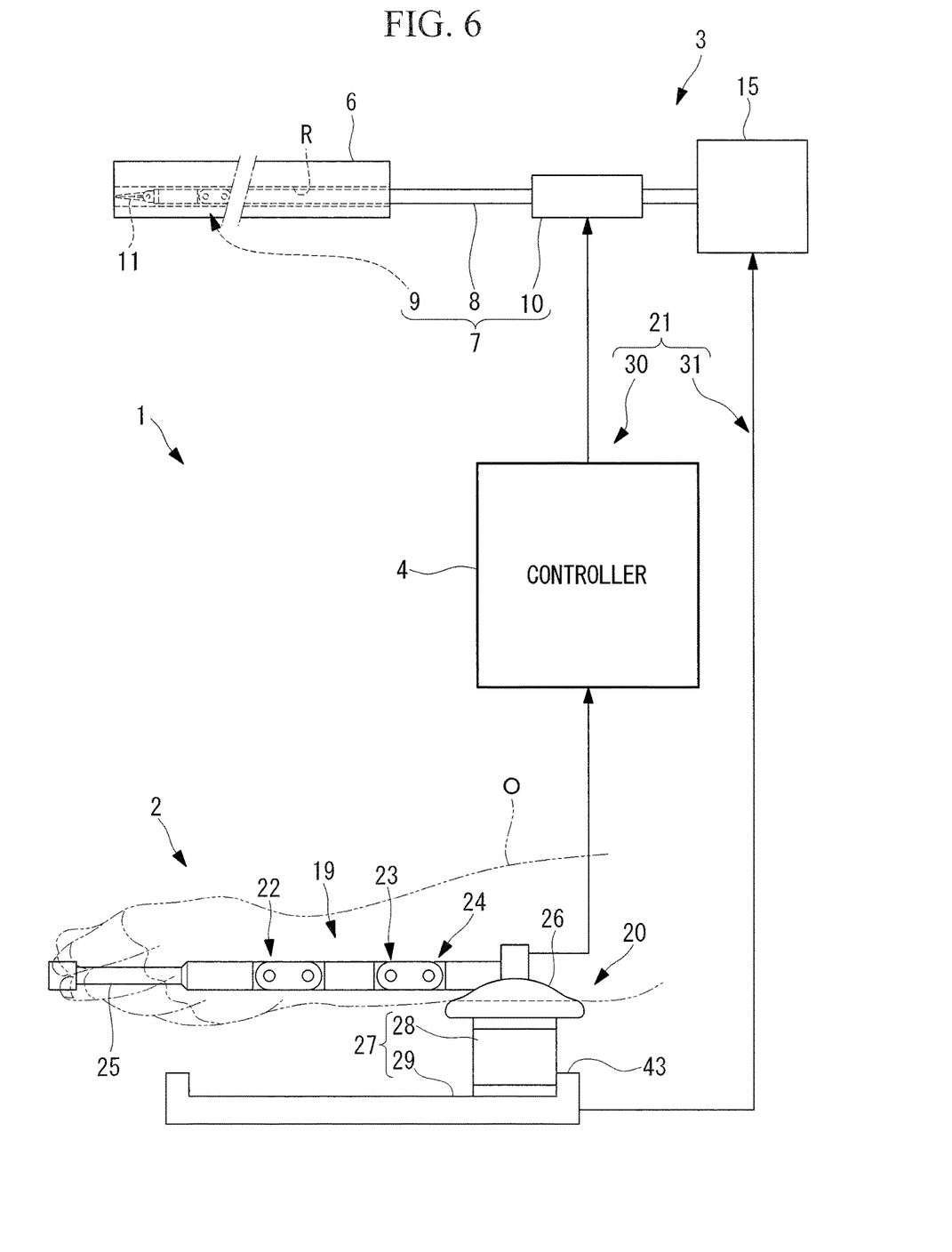
FIG. 6 is a diagram showing a modification of the medical manipulator system shown in FIG. 2.

In addition, as shown in FIG. 6, a stopper 43 for limiting the movable range of the slider 28 of the operation input device 2 may be provided, and a positional relationship may be set such that the distal end of the gripping forceps 11 is completely accommodated within the channel R of the insertion portion 6 when the slider 28 is moved backwards as much as possible until it is brought into contact with the stopper 43.

With such a configuration, the distal end of the gripping forceps 11 does not protrude from the insertion portion 6 when the medical manipulator 3 is inserted into a body cavity, and it is possible to prevent the gripping forceps 11 from coming into contact with an inner wall of the body cavity. In addition, when the operator O is trying to change a viewing field by moving only the distal end of the insertion portion 6 (endoscope distal end), accidental contact between the medical manipulator 3 and surrounding organs can be prevented.

Figure 7:
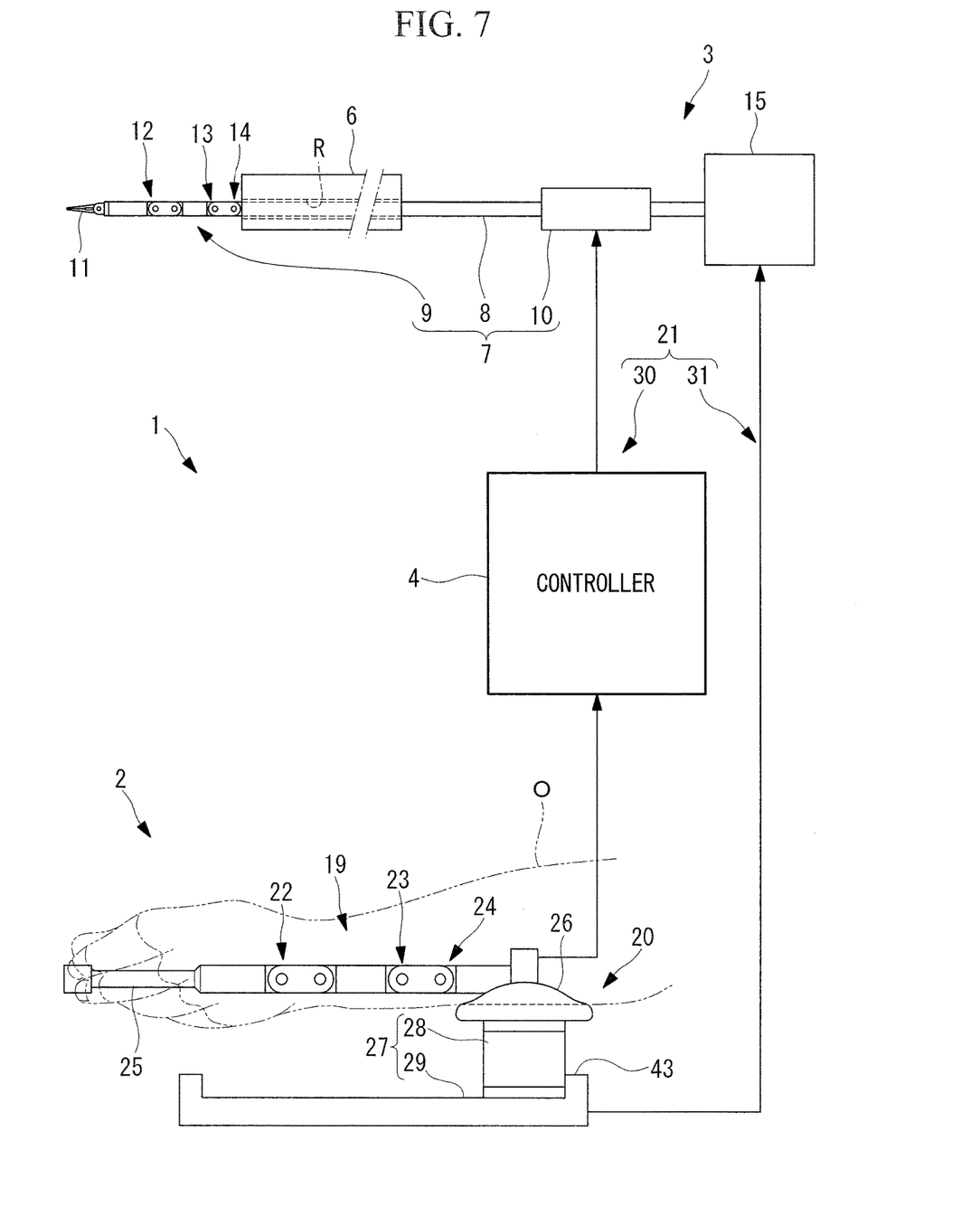
FIG. 7 is a diagram showing another modification of the medical manipulator system shown in FIG. 2.

Conversely, as shown in FIG. 7, a positional relationship may be set such that the entire movable portion 9 is completely exposed from the distal end of the insertion portion 6 when the slider 28 of the operation input device 2 is moved backwards as much as possible until it is brought into contact with the stopper 43. With such a configuration, the movable portion 9 is pulled into the channel R in a curved state, and thereby, it is possible to prevent the occurrence of failure due to contact with an edge of the channel R on the distal-end side.

As a result, the above-described embodiment leads to the following aspects.

One aspect of the present invention is an operation input device for inputting an operation command to a medical manipulator having a distal-end-side moving portion having at least one joint on a distal end and a proximal-end-side moving portion that is connected to a proximal-end side of the distal-end-side moving portion and moves the distal-end-side moving portion, the device comprising: a first operation portion that generates a moving command for driving the distal-end-side moving portion in accordance with an operation command input with a palm or a finger; and a second operation portion that is linked to the first operation portion and generates a moving command for driving the proximal-end-side moving portion in accordance with an operation command input with a wrist or an arm.

With the operation input device according to this aspect, the distal-end-side moving portion is driven by the moving command generated in accordance with the operation command that has been input with the palm or fingers of an operator, and the proximal-end-side moving portion is driven by the moving command generated in accordance with the operation command that has been input with the wrist or arm of the same operator. Because the distal-end-side moving portion is a portion that finally sets the distal end position of the medical manipulator, the distal-end-side moving portion is precisely driven by inputting a precise operation command with the palm or fingers of the operator. In particular, in a case in which treatment is carried out on an affected part at a fine scale by using a treatment portion provided on the distal end of the medical manipulator, the treatment can be precisely carried out by inputting the precise operation command with the palm or fingers of the operator.

On the other hand, because the proximal-end-side moving portion is a portion that moves the entire distal-end-side moving portion of the medical manipulator, the movement may be rough. Therefore, the proximal-end-side moving portion is driven by a rough operation command input with the wrist or arm of the operator, and thereby, the entire distal-end-side moving portion can be roughly positioned. In other words, in accordance with coarse movement and fine movement, the operation commands for the joints with different response speeds can be input to separate input systems with separate parts of the hands of the operator without an unintuitive feeling, and thereby, it is possible to facilitate the operation of the medical manipulator.

In the operation input device according to the above-mentioned aspect, the distal-end-side moving portion may be driven electrically; the proximal-end-side moving portion may be driven mechanically; the first operation portion may generate the moving command so as to be formed of an electric signal; and the second operation portion may generate the moving command so as to be formed of a mechanical driving force.

In accordance with this configuration, the proximal-end-side moving portion, which undergoes large-scale movement such that the entire distal-end-side moving portion is moved, can be manually operated by using the mechanical driving force generated by the second operation portion, and fine-scale movement of the distal-end-side moving portion that finally sets the distal end position can be carried out by the electrical operation using the electrical signal. In particular, by manually operating the portion that undergoes the large-scale movement, the operator can easily recognize a repulsive force caused by interference with body tissue and can avoid the interference at an earlier stage.

In the operation input device according to the above-mentioned aspect, the second operation portion may drive the proximal-end-side moving portion and generate a mechanical driving force for at least advancing and retracting the distal-end-side moving portion.

With this configuration, the largest advancing/retracting movement can be achieved by the manual operation, and the operator can easily recognize a repulsive force generated by interference between that portion and body tissue.

In addition, another aspect of the present invention is a medical manipulator system comprising any of the operation input devices described above and a medical manipulator that is operated by the operation input device.

The present invention affords an advantage in that it is possible to input operation commands for joints with different response speeds without an unintuitive feeling and to facilitate the operation of a medical manipulator.

REFERENCE SIGNS LIST 1 medical manipulator system
2 operation input device
3 medical manipulator
7 distal-end-side moving portion
12, 13, 14 joint
15 proximal-end-side moving portion
19 first operation portion
20 second operation portion

The invention claimed is:

1. An operation input device for inputting an operation command to a medical manipulator provided with an insertion portion that is inserted into a body of a patient, a channel that is formed so as to penetrate through the insertion portion in a longitudinal direction, an elongated portion that advances and retracts in the channel while being kept in contact with an inner wall of the channel at least one joint that is provided on a distal end of the elongated portion, a treatment portion that is provided on a distal-end side of the joint so as to be movable in response to a movement of the joint, a moving portion that is connected to a proximal-end side of the elongated portion and that advances and retracts the elongated portion, and a driving unit that is disposed at the proximal-end side of the elongated portion and that drives the joint of the elongated portion, the operation input device comprising:
   a first operation portion that generates an electrical signal in accordance with an operation by a palm or a finger of an operator;
   a controller that receives the electrical signal and controls the driving unit on the basis of the electrical signal;
   a second operation portion that is linked to the first operation portion and generates a mechanical motive force in accordance with the operation by the wrist or the arm of the operator; and
   a mechanical-motive-force transmitting portion that transmits the mechanical driving force generated at the second operation portion to the moving portion.

2. A medical manipulator system provided with
   a medical manipulator that is inserted into a body of a patient and carries out treatment, and
   an operation input device for inputting an operation command to the medical manipulator,
   wherein the medical manipulator comprises:
   an insertion portion that is inserted into the body of the patient;
   a channel that is formed so as to penetrate through the insertion portion in a longitudinal direction;
   an elongated portion that advances and retracts in the channel while being kept in contact with an inner wall of the channel;
   at least one joint that is provided on a distal end of the elongated portion;
   a treatment portion that is provided on a distal-end side of the joint so as to be movable by a movement of the joint;
   a moving portion that is connected to the proximal-end side of the elongated portion and advances and retracts the elongated portion; and
   a driving unit that is disposed at the proximal-end side of the elongated portion and drives the joint of the elongated portion; and wherein
   the operation input device comprises:
      a first operation portion that generates an electrical signal in accordance with an operation by a palm or finger of an operator;
      a controller that receives the electrical signal generated at the first operation portion and controls the driving unit on the basis of the electrical signal;
      a second operation portion that is linked to the first operation portion and generates a mechanical motive force in accordance with an operation by the wrist or the arm of the operator; and
   a mechanical-motive-force transmitting portion that transmits the mechanical driving force generated at the second operation portion to the moving portion.

* * * * *